(12) United States Patent
Norris

(10) Patent No.: US 9,606,055 B2
(45) Date of Patent: *Mar. 28, 2017

(54) SYSTEMS AND METHODS FOR STATISTICAL MEASUREMENT CONTROL OF SPECTROPHOTOMETRIC DATA

(71) Applicant: PPG Industries Ohio, Inc., Cleveland, OH (US)

(72) Inventor: Alison M. Norris, Avon, OH (US)

(73) Assignee: PPG Industries Ohio, Inc., Cleveland, OH (US)

( * ) Notice: Subject to any disclaimer, the term of this patent is extended or adjusted under 35 U.S.C. 154(b) by 899 days.

This patent is subject to a terminal disclaimer.

(21) Appl. No.: 13/737,179

(22) Filed: Jan. 9, 2013

(65) Prior Publication Data

US 2014/0195189 A1    Jul. 10, 2014

(51) Int. Cl.
| | |
|---|---|
| G01N 21/55 | (2014.01) |
| G01J 3/50 | (2006.01) |
| G01N 21/25 | (2006.01) |
| G01N 21/84 | (2006.01) |
| G01N 21/88 | (2006.01) |
| G01J 3/46 | (2006.01) |

(52) U.S. Cl.
CPC .............. *G01N 21/55* (2013.01); *G01J 3/462* (2013.01); *G01J 3/504* (2013.01); *G01N 21/255* (2013.01); *G01N 21/8422* (2013.01); *G01N 21/8851* (2013.01); *G01N 2021/8877* (2013.01); *G01N 2201/1245* (2013.01); *G01N 2201/1248* (2013.01)

(58) Field of Classification Search
USPC .......................................................... 702/104
See application file for complete search history.

(56) References Cited

U.S. PATENT DOCUMENTS

| | | | |
|---|---|---|---|
| 5,606,164 A | 2/1997 | Price et al. | |
| 8,879,066 B2 * | 11/2014 | Norris ................... | G01N 21/25 356/445 |

(Continued)

FOREIGN PATENT DOCUMENTS

| | | |
|---|---|---|
| DE | 102008009302 A1 | 7/2009 |
| WO | 00/63676 A1 | 10/2000 |

(Continued)

OTHER PUBLICATIONS

Stuart L. Cantor, NIR Spectroscopy Applications in the Development of a Compacted Multiparticulate System for Modified Release, AAPS PharmSciTech, vol. 12, No. 1, Mar. 2011 (# 2011), 17 pages.*

(Continued)

*Primary Examiner* — Tung Lau
(74) *Attorney, Agent, or Firm* — Michael J. Frodsham; W. Brad Barger

(57) ABSTRACT

A computer implemented method. The method includes obtaining, using a processor, spectral reflectance data from a coated surface having a target coating theron; and determining, using the processor, whether the data includes any outlier data points. The method also includes removing, using the processor, at least one of the outlier data points to produce final spectral reflectance data; and calculating, using the processor, a characteristic of the target coating based at least in part on the final spectral reflectance data.

11 Claims, 2 Drawing Sheets

(56) References Cited

U.S. PATENT DOCUMENTS

| | | | |
|---|---|---|---|
| 2005/0018173 A1 | 1/2005 | Udo et al. | |
| 2009/0213120 A1* | 8/2009 | Nisper | G01J 3/504 345/426 |
| 2014/0267227 A1* | 9/2014 | Norris | G01J 3/504 345/419 |
| 2014/0278251 A1* | 9/2014 | Norris | G06F 19/703 702/189 |
| 2015/0134269 A1* | 5/2015 | Norris | G01N 21/251 702/28 |
| 2015/0134300 A1* | 5/2015 | Norris | G01N 21/25 702/189 |

FOREIGN PATENT DOCUMENTS

| | | |
|---|---|---|
| WO | 2009065956 | 5/2009 |
| WO | WO2009/065956 | 5/2009 |
| WO | WO2009/065956 A2 | 5/2009 |

OTHER PUBLICATIONS

Jeffrey R. Johnson, Radiative transfer modeling of dust-coated Pancam calibration target materials: Laboratory visible/near-infrared spectrogoniometry, Journal of Geophysical Research, vol. 111, E12S07, doi:10.1029/2005JE002658, 2006, 22 pages.*

Canadian Office Action and Search Report for App. 2,897,061 mailed Jul. 15, 2016.

* cited by examiner

US 9,606,055 B2

SYSTEMS AND METHODS FOR STATISTICAL MEASUREMENT CONTROL OF SPECTROPHOTOMETRIC DATA

FIELD OF THE INVENTION

In various embodiments, the present invention generally relates to a method and apparatus for deriving accurate data obtained from spectrophotometric measurements of a surface that is coated by a cured complex coating (e.g., paint) mixture.

BACKGROUND OF INVENTION

Because of inherent variations of color across a coated surface, which may be due to, for example, poor coating applications, unstable paint chemistries, natural fluctuations of special pigments such as micas and xirallics, statistical measurement control ("SMC") is often employed to remove errant or inaccurate data that result from such variations. Also, SMC is often used to ameliorate the effects of measuring an erroneous area or an area that is not representative of the rest of the coated surface that is being measured. Such areas of concern include, for example, scratches in the surface, dust, fingerprints, coating defects, or areas in which the spectrophotometer aperture is not kept fully on the coating.

Typically, SMC has been completed using colorimetric data (e.g., as L*, a*, and b*) on an angular basis using confidence intervals with rigid requirements. However, such methods are not always accurate in removing errant or inaccurate data obtained from spectrophotometric measurements. Thus, there is a need for systems and methods that use spectral reflectance data, instead of colorimetric derivations, and that allow for flexible tolerances.

SUMMARY OF INVENTION

In a first aspect, embodiments of the invention provide a computer implemented method. The method includes obtaining, using a processor, spectral reflectance data from a coated surface having a target coating theron; and determining, using the processor, whether the data includes any outlier data points. The method also includes removing, using the processor, at least one of the outlier data points to produce final spectral reflectance data; and calculating, using the processor, a characteristic of the target coating based at least in part on the final spectral reflectance data. In another aspect, embodiments of the invention provide a system. The system includes a user interface; and a processor in communication with the user interface. The processor is programmed to obtain spectral reflectance data, from a coated surface having a target coating theron; determine whether the data includes any outlier data points; remove at least one of the outlier data points to produce final spectral reflectance data; and calculate a characteristic of the target coating based at least in part on the final spectral reflectance data.

In another aspect embodiments of the invention provide an apparatus. The apparatus includes means for obtaining spectral reflectance data from a coated surface having a target coating theron; means for determining whether the data includes any outlier data points; means for removing at least one of the outlier data points to produce final spectral reflectance data; and means for calculating a characteristic of the target coating based at least in part on the final spectral reflectance data. In another aspect, embodiments of the invention provide a non-transitory computer readable medium including software for causing a processor to:
- obtain spectral reflectance data from a coated surface having a target coating theron;
- determine whether the data includes any outlier data points;
- remove at least one of the outlier data points to produce final spectral reflectance data; and
- calculate a characteristic of the target coating based at least in part on the final spectral reflectance data.

DETAILED DESCRIPTION OF THE INVENTION

In various aspects, embodiments of the invention include a spectrophotometer and a method that may be used to generate accurate data from data obtained from spectrophotometric measurements of a coated surface. Various embodiments of the invention include an apparatus that has a device for capturing spectrophotometric data for a target sample and a processor for deriving accurate data from the spectrophotometric data that can be used to produce a coating having characteristics that are similar to the target sample. An output device may be used for conveying the characteristics to a user.

While the description herein generally refers to paint, it should be understood that the devices, systems and methods apply to other types of coatings, including stain and industrial coatings. The described embodiments of the invention should not be considered as limiting. A method consistent with the present invention may be practiced in a variety of fields such as the matching and/or coordination of apparel and fashion products.

Embodiments of the invention may be used with or incorporated in a computer system that may be a stand alone unit or include one or more remote terminals or devices in communication with a central computer via a network such as, for example, the Internet or an intranet. As such, the computer or "processor" and related components described herein may be a portion of a local computer system or a remote computer or an on-line system or combinations thereof. The database and software described herein may be stored in computer internal memory or in a non-transitory computer readable medium.

Embodiments of the present invention are directed to a multi-step process for statistical measurement control ("SMC") of data obtained from a spectrophotometer.

Figure 1:
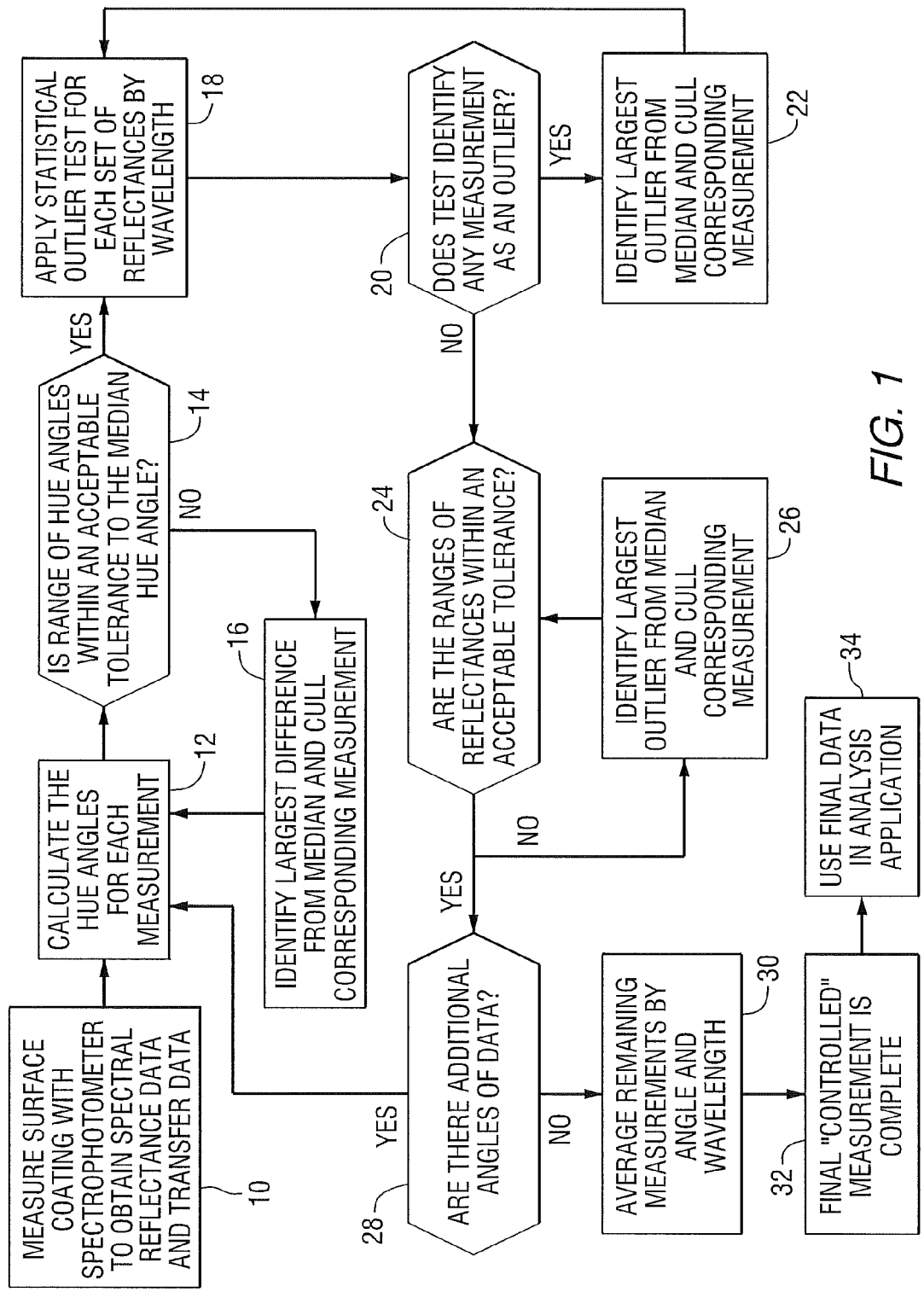
FIG. 1 illustrates a flowchart of an embodiment of a process for deriving data obtained from spectrophotometric measurements of a surface that is coated by a cured complex coating (e.g., paint) mixture.
Figure 2:
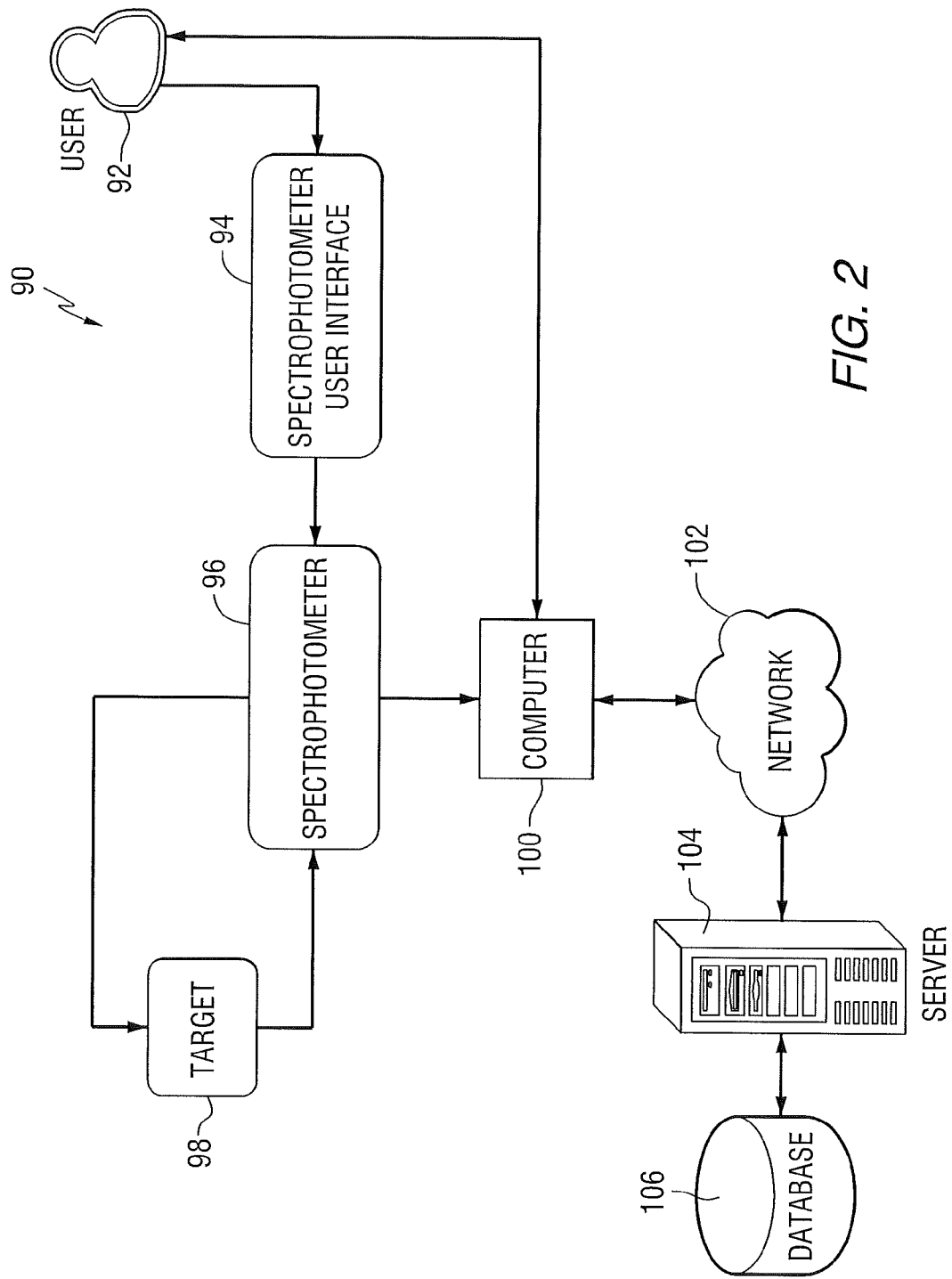
FIG. 2 illustrates an embodiment of a system which may be used to generate data obtained from spectrophotometric measurements of a surface that is coated by a cured complex coating (e.g., paint) mixture.

FIG. 1 illustrates a flowchart of an embodiment of a process for deriving data obtained from spectrophotometric measurements of a coated surface. The process begins at step 10 when a user initiates the transfer (e.g., an upload) of spectral reflectance data from an optical instrument, such as a spectrophotometer. In various embodiments, the data are transferred either after each individual measurement or as a series of measurements after all measurements have been completed. In various embodiments, at least three measurements are taken to ensure an adequate sample, and in various embodiments, the maximum number of measurements is based on a user-specified number of measurements.

In order to obtain accurate measurements at step 10, it may be desirable that the spectrophotometer remain in a singular orientation, relative to the coated surface, no matter the location of the measurement on the surface. Also, it may be desirable in various embodiments to move the spectrophotometer to different locations across the target surface to obtain multiple measurements and it may further be desirable to avoid obvious defects on the target surface, such as dirt, scratches, pinholes, blisters, etc.

At step 12 of the process the hue angle for each measurement taken at step 10 is calculated. Such calculation eliminates one or multiple measurements that are clearly not close to the majority of measurements when for example, a measurement is taken of a different surface than the target surface. In various embodiments, the underlying assumption is made that the majority of measurements from step 10 are correct. If a multi-angle spectrophotometer device is employed at step 10, the hue angle at the "face" angle (e.g., the 45 degree angle) may be used. At step 14, each measurement is compared to the median hue angle. At step 16, if it is determined that the difference between the median hue angle and the hue angle of an individual measurement is larger than a specified tolerance, the measurement is marked for exclusion. In various embodiments, the specified tolerance is, for example, 5 degrees and, in various embodiments setting the tolerance requires an individual angular analysis. In various embodiments, if multiple measurements exceed the tolerance, at step 16 the measurement with the largest difference is marked for exclusion. In various embodiments, steps 12, 14 and 16 are repeated as needed for largely varying data sets. However, if a minimum number of measurements (e.g., three measurements) has been reached at the time of hue angle analysis and a difference larger than the tolerance is present as determined at step 14, the measurements will fail the process and can be addressed as described hereinbelow.

Once all checks of the hue angle versus the median hue angle are complete and within a desired tolerance level as determined at step 14, the process advances to step 18 where a statistical outlier detection test is applied. In various embodiments, the statistical outlier detection test is the Grubbs' test for outliers. In various embodiments, the assumption is made that a normal distribution of measurements is present because measurements that skew the normality of the measurements were eliminated at step 16. In various embodiments, the Grubbs' test is applied to the spectral reflectance data at each specific angle and wavelength combination. In terms of statistics, the Grubbs' test uses a significance level, derived from a confidence level, in order to accept or reject the null and alternative hypotheses. In various embodiments, the null hypothesis is that the spectral reflectance data set at a particular angle and wavelength combination does not contain any outliers. The alternative hypothesis follows that there is at least one outlier in the data set. To complete the analysis, the confidence level and significance level are set based on process needs. The "G" value and "critical" value ("C") are calculated as follows in equations (1) and (2):

$$G = \frac{|R - M|}{S} \quad (1)$$

$$C = \left(\frac{N-1}{\sqrt{N}}\right) * \sqrt{\frac{t^2}{N-2+t^2}} \quad (2)$$

where R is the spectral reflectance of the specific measurement at the specific angle and wavelength combination, M is the median value of the spectral reflectances from all measurements not already marked for exclusion at the specific angle and wavelength combination, S is the standard deviation of the spectral reflectances from all measurements not marked for exclusion at the specific angle and wavelength combination (calculated based on the median), t is the two-sided Student's t-value at the desired significance level, and N is the number of measurements not already marked for exclusion. When the value is larger than the C value, the null hypothesis is rejected and the alternate hypothesis is accepted. Otherwise, the null hypothesis is accepted. For any scenario where the null hypothesis is rejected, the particular angle and wavelength combination may be marked as a potential outlier at step 20. Then, for each measurement, the number of angle and wavelength combinations that have been marked as potential outliers at step 20 are counted. If the count exceeds a desired tolerance, the measurement is marked for exclusion. In various embodiments, the tolerance is, for example, 10 percent of the total evaluations and, in various embodiments setting the tolerance requires an individual angular analysis. If more than one measurement exceeds the desired tolerance, the measurement with the largest count of potential outliers is marked for exclusion at step 22. Steps 18, 20 and 22 may be repeated as needed or until a minimum number of measurements (e.g., three measurements) has been reached. If the minimum number of measurements has been reached and the statistical outlier test identifies another measurement for exclusion, the process fails and can be addressed as described hereinbelow.

Once the measurements which have not been marked for exclusion pass the statistical outlier test and/or the minimum number of measurements has been reached, the process continues to step 24. At step 24 a range check of the remainder spectral reflectances at the specific angle and wavelength combination is made against a tolerance value. In various embodiments, the tolerance is, for example, 1/100 with respect to the given range of potential reflectance values and, in various embodiments setting the tolerance requires an individual angular analysis. In various embodiments, one purpose of the range check is to compensate for the statistical outlier test potentially being overly strict. In such a case, the final range check of spectral reflectances will allow a measurement to pass and complete the process, even if the statistical outlier test may have continued to identify more outliers after the reaching the minimum number of measurements, which may cause a failure in the process absent a final rang check. Also, in the case of extreme variations of measurements and/or data, the statistical outlier test may be "fooled" into accepting poor measurements due to a large standard deviation calculation. In such a situation, the potential problem is the use of errant data to create the final controlled measurement. Both scenarios may be handled using the range check of the spectral reflectances at step 24. In various embodiments, the range, or maximum minus minimum, is computed at step 24 for the spectral reflectances of all measurements not already excluded at each specific angle and wavelength combination. The range is then compared to the desired tolerance. If the computed range value exceeds the tolerance, the largest single offending measurement within the range calculation is marked as a potential outlier. In various embodiments, the largest single offending measurement will be the maximum value or the minimum value. After all ranges are checked against the tolerance at step 24, a count is taken of how many angle and wavelength combinations for each measurement have been marked as potential outliers. If the count exceeds a desired tolerance, the measurement may be excluded at step 26 and in various embodiments the process returns to step 18 (if more than the minimum number of unexcluded measurements remain) or returns to step 24 so that the spectral reflectance range check is performed again. In various embodiments, the tolerance is, for example, 10% of the total evaluations and, in various embodiments setting the tolerance requires an individual angular analysis. If the minimum number of measurements is reached but the spectral reflectance range check fails, the process fails and can be addressed as described hereinbelow. If the minimum number of measurements has been met and the spectral reflectance range check passes, the process advances to step 28, where the process determines whether additional angles of data need to be processed, in which case the process returns to step 12.

If there are no additional angles of data that need to be processed as determined at step 28, in various embodiments the individual angular measurements are consolidated into a single angular measurement for each angle assessed at step 30. In various embodiments, the measurements are consolidated by calculating an average of all the remaining (i.e., acceptable) measurements at each specific angle and wavelength combination. The final result at 32 is a set of spectral reflectance data that is substantially stable and reliable and that can be used as a baseline in future calculations at step 34 for various applications while working with the same coated surface for which the spectrophotometric data were obtained at step 10. For example, the final result may be used for determination of a characteristic of the coated surface, generation of colorimetric data (L*, a*, b*, C*, h*), generation of tristimulus data (X, Y, Z), generation of absorption and scattering data (K, S), opacity calculations, travel calculations, image rendering, digital chip organization/ordering, printed color tool organization/ordering, jetness calculations, pigment strength calculations, database searching, quality control of input data into a database, quality control of instrument output, quality control of printed color tools, alignment of multiple instruments, color formulations, color match quality indicator, color adjustment, spectral reflectance curve comparisons, variant prediction/selection, and any other appropriate application.

In the event that a set of measurements fail the process illustrated in FIG. 1, in various embodiments the failure can be handled in three ways. First, additional measurements may be taken with the spectrophotometer and then added to the already-existing data set of measurements. The process would then begin at step 12 with an augmented data set. Second, the current data set may be discarded and the process started again at step 12 with a new data set. Third, the process of FIG. 1 may be skipped altogether with the understanding that variations in the target surface may introduce noise into the spectral reflectance data or subsequent colorimetric derivations.

Provided below is an example of an embodiment of the process described herein used with six spectrophotometric measurements made at a single angle. Table 1 illustrates the starting data.

TABLE 1

Starting Data

| Wavelength | Measurement 1 | Measurement 2 | Measurement 3 | Measurement 4 | Measurement 5 | Measurement 6 |
| --- | --- | --- | --- | --- | --- | --- |
| 400 | 10.46 | 10.98 | 11.52 | 10.31 | 11.01 | 11.13 |
| 410 | 10.74 | 11.3 | 11.84 | 10.6 | 11.31 | 11.43 |
| 420 | 11.13 | 11.73 | 12.24 | 10.98 | 11.76 | 11.85 |
| 430 | 11.71 | 12.33 | 12.82 | 11.56 | 12.37 | 12.45 |
| 440 | 12.48 | 13.15 | 13.63 | 12.32 | 13.19 | 13.25 |
| 450 | 13.74 | 14.44 | 14.91 | 13.59 | 14.48 | 14.54 |
| 460 | 15.59 | 16.35 | 16.79 | 15.43 | 16.41 | 16.43 |
| 470 | 18.14 | 18.92 | 19.33 | 17.99 | 19 | 19 |
| 480 | 21.75 | 22.55 | 22.88 | 21.59 | 22.59 | 22.59 |
| 490 | 26.52 | 27.1 | 27.4 | 26.35 | 27.17 | 27.14 |
| 500 | 31.06 | 31.22 | 31.45 | 30.88 | 31.29 | 31.27 |
| 510 | 33.93 | 33.49 | 33.69 | 33.76 | 33.57 | 33.54 |
| 520 | 34.23 | 33.21 | 33.39 | 34.05 | 33.25 | 33.25 |
| 530 | 31.97 | 30.69 | 30.88 | 31.81 | 30.74 | 30.73 |
| 540 | 28.75 | 27.39 | 27.63 | 28.62 | 27.46 | 27.46 |
| 550 | 25.8 | 24.47 | 24.72 | 25.67 | 24.51 | 24.51 |
| 560 | 23.01 | 21.75 | 22.04 | 22.92 | 21.81 | 21.81 |
| 570 | 20.76 | 19.58 | 19.89 | 20.69 | 19.63 | 19.64 |
| 580 | 19.01 | 17.88 | 18.23 | 18.93 | 17.94 | 17.95 |
| 590 | 17.64 | 16.57 | 16.93 | 17.57 | 16.62 | 16.64 |
| 600 | 16.59 | 15.56 | 15.94 | 16.51 | 15.61 | 15.63 |
| 610 | 15.83 | 14.83 | 15.21 | 15.76 | 14.89 | 14.91 |
| 620 | 15.31 | 14.33 | 14.73 | 15.24 | 14.4 | 14.42 |
| 630 | 15 | 14.04 | 14.43 | 14.93 | 14.1 | 14.12 |
| 640 | 14.91 | 13.95 | 14.34 | 14.83 | 14.01 | 14.03 |
| 650 | 14.97 | 14.01 | 14.4 | 14.89 | 14.07 | 14.09 |
| 660 | 15.25 | 14.29 | 14.68 | 15.18 | 14.34 | 14.37 |
| 670 | 15.67 | 14.69 | 15.07 | 15.61 | 14.74 | 14.76 |
| 680 | 16.37 | 15.36 | 15.73 | 16.3 | 15.41 | 15.44 |
| 690 | 17.3 | 16.24 | 16.6 | 17.23 | 16.3 | 16.31 |
| 700 | 18.36 | 17.2 | 17.54 | 18.29 | 17.26 | 17.28 |

Hue angle analysis (step 12) marks Measurement 4 for exclusion. The hue angle analysis is recycled a second time and marks Measurement 1 for exclusion. The hue angle analysis is recycled a third time and all remaining measurements fall within the tolerance.

The outlier test (in this case the Grubb's test for outliers) follows next (step 18). The Grubbs test marks Measurement 3 for exclusion. When the Grubbs' test is recycled, a minimum of three measurements is met, so the analysis is not performed again.

Because the minimum number of measurements has been reached, the range check step (step 24) is started with the measurements not already marked for exclusion. The range check accepts the final three measurements.

The unexcluded measurements are finally averaged as the final working output as shown in Table 2.

TABLE 2

| Wavelength | SMC Final Measurement |
|---|---|
| 400 | 0.1104 |
| 410 | 0.1135 |
| 420 | 0.1178 |
| 430 | 0.1238 |
| 440 | 0.132 |
| 450 | 0.1449 |
| 460 | 0.164 |
| 470 | 0.1897 |
| 480 | 0.2258 |
| 490 | 0.2714 |
| 500 | 0.3126 |
| 510 | 0.3353 |
| 520 | 0.3324 |
| 530 | 0.3072 |
| 540 | 0.2744 |
| 550 | 0.245 |
| 560 | 0.2179 |
| 570 | 0.1962 |
| 580 | 0.1792 |
| 590 | 0.1661 |
| 600 | 0.156 |
| 610 | 0.1488 |
| 620 | 0.1438 |
| 630 | 0.1409 |
| 640 | 0.14 |
| 650 | 0.1406 |
| 660 | 0.1433 |
| 670 | 0.1473 |
| 680 | 0.154 |
| 690 | 0.1628 |
| 700 | 0.1725 |

FIG. 6 illustrates an embodiment of a system 90 which may be used to identify physical property attributes of a coating mixture of a target sample. A user 92 may utilize a user interface 94, such as a graphical user interface, to operate a spectrophotometer 96 to measure the properties of a target sample 98. The data from the spectrophotometer 96 may be transferred to a computer 100, such as a personal computer, a mobile device, or any type of processor. The computer 100 may be in communication, via a network 102, with a server 104. The network 102 may be any type of network, such as the Internet, a local area network, an intranet, or a wireless network. The server 104 is in communication with a database 106 that may store the data and information that is used and generated by the methods of embodiments of the present invention. Various steps of the methods of embodiments of the present invention may be performed by the computer 100 and/or the server 106.

In another aspect, the invention may be implemented as a non-transitory computer readable medium containing software for causing a computer or computer system to perform the method described above. The software can include various modules that are used to enable a processor and a user interface to perform the methods described herein.

It will be readily appreciated by those skilled in the art that modifications may be made to the invention without departing from the concepts disclosed in the forgoing description. Such modifications are to be considered as included within the following claims unless the claims, by their language, expressly state otherwise. Accordingly, the particular embodiments described in detail herein are illustrative only and are not limiting to the scope of the invention which is to be given the full breadth of the appended claims and any and all equivalents thereof.

What is claimed is:

1. A computer implemented data processing method, comprising:
   obtaining from a coating analysis device multiple measurements of spectral reflectance data from a coated surface having a target coating thereon;
   a computer system performing, using a processor, a statistical outlier test on the multiple measurements of spectral reflectance data, wherein the statistical outlier test comprises:
   calculating a statistical analysis of the multiple measurements of spectral reflectance data at each respective angle and wavelength combination within each measurement,
   determining a total number of potential statistical outliers associated with the multiple measurements of spectral reflectance data at each respective angle and wavelength combination for each respective measurement, and
   when the total number of potential statistical outliers for a particular measurement exceeds a tolerance, generating final spectral reflectance data by excluding data from the particular measurement;
   removing, using the processor, at least a portion of the spectral reflectance data within the final spectral reflectance data that falls outside of a pre-defined acceptable tolerance range; and
   calculating, using the processor, a characteristic of the target coating based at least in part on the final spectral reflectance data.

2. The method of claim 1, wherein the statistical outlier test is the Grubb's test for outliers.

3. The method of claim 1, wherein calculating a characteristic of the target coating includes at least one of generating colorimetric data (L*, a*, b*, C*, h*), generating tristimulus data (X, Y, Z), generating absorption and scattering data (K, S), calculating opacity, calculating jetness, calculating pigment strength, generating color formulations, generating a color match quality indicator, generating a color adjustment, and generating spectral reflectance curve comparisons.

4. The method of claim 1, further comprising measuring the coated surface with a spectrophotometer to obtain the multiple measurements spectral reflectance data.

5. A non-transitory computer readable medium including data processing software for causing a processor to:
   obtain, from a coating analysis device, multiple measurements of spectral reflectance data from a coated surface having a target coating thereon;
   perform, using the processor, a statistical outlier test on the multiple measurements of spectral reflectance data, wherein the statistical outlier test comprises:
   calculating a statistical analysis of the multiple measurements of spectral reflectance spectral reflectance data at each respective angle and wavelength combination within each measurement, determining a total number of potential statistical outliers associated with the multiple measurements of spectral reflectance data at each respective angle and wavelength combination for each respective measurement, and generating final spectral reflectance data by excluding measurements that are associated with a total number of potential statistical outliers that exceeds a particular threshold; and calculate a characteristic of the target coating based at least in part on the final spectral reflectance data.

6. The computer readable medium of claim 5, wherein the computer readable medium includes software for causing the processor to remove at least one of the outlier data points to produce the final spectral reflectance data using the Grubb's test for outliers.

7. A system, comprising:

a user interface; and a processor in communication with the user interface and programmed to:

obtain, from a coating analysis device, multiple measurements of spectral reflectance data from a coated surface having a target coating thereon;

perform, using the processor, a statistical outlier test on the multiple measurements of spectral reflectance data, wherein the statistical outlier test comprises:

calculating a statistical analysis of the multiple measurements of spectral reflectance data at each respective angle and wavelength combination within each measurement, determining a total number of potential statistical outliers associated with the multiple measurements of spectral reflectance data for each respective measurement, and when the total number of potential statistical outliers for a particular measurement exceeds a tolerance, generating final spectral reflectance data by excluding data from the particular measurement; and calculate a characteristic of the target coating based at least in part on the final spectral reflectance data.

8. The system of claim 7, further comprising a database in communication with the processor.

9. The system of claim 7, further comprising a display in communication with the processor.

10. The system of claim 7, further comprising a spectrophotometer in communication with the processor.

11. The system of claim 7, wherein the processor is programmed to determine whether the data includes any outlier data points using the Grubb's outlier test.

* * * * *